US012496438B2

(12) United States Patent
Shapiro et al.

(10) Patent No.: US 12,496,438 B2
(45) Date of Patent: Dec. 16, 2025

(54) APPARATUS COMPRISING DIELECTRIC LAYER COUPLED TO ANISOTROPIC LAYER

(71) Applicant: NOVOCURE GMBH, Root (CH)

(72) Inventors: David Shapiro, Haifa (IL); Yoram Wasserman, Haifa (IL); Stas Obuchovsky, Haifa (IL)

(73) Assignee: NOVOCURE GMBH, Baar (CH)

( * ) Notice: Subject to any disclaimer, the term of this patent is extended or adjusted under 35 U.S.C. 154(b) by 307 days.

(21) Appl. No.: 18/342,774

(22) Filed: Jun. 28, 2023

(65) Prior Publication Data

US 2023/0414931 A1 Dec. 28, 2023

Related U.S. Application Data

(60) Provisional application No. 63/356,228, filed on Jun. 28, 2022.

(51) Int. Cl.
*A61N 1/04* (2006.01)
*A61N 1/36* (2006.01)

(52) U.S. Cl.
CPC ........ *A61N 1/0496* (2013.01); *A61N 1/36002* (2017.08)

(58) Field of Classification Search
None
See application file for complete search history.

(56) References Cited

U.S. PATENT DOCUMENTS

| | | | | |
|---|---|---|---|---|
| 5,571,165 A * | 11/1996 | Ferrari | A61N 1/0492 607/152 |
| 2005/0222647 A1* | 10/2005 | Wahlstrand | A61N 1/06 607/45 |
| 2009/0076366 A1 | 3/2009 | Palti | |
| 2010/0198044 A1 | 8/2010 | Gehman et al. | |
| 2013/0066412 A1* | 3/2013 | Van Der Beek | A61N 1/0492 607/152 |
| 2021/0052884 A1* | 2/2021 | Jashek | A61N 1/0456 |
| 2021/0402179 A1 | 12/2021 | Wasserman et al. | |

FOREIGN PATENT DOCUMENTS

JP 2006/297602 11/2006

OTHER PUBLICATIONS

International Search Report and Written Opinion were mailed on Oct. 16, 2023 by the International Searching Authority for International Application No. PCT/IB2023/056697 filed on Jun. 28, 2023 and published as WO2024003775 (Applicant—Novocure Gmbh) (8 pages).

* cited by examiner

*Primary Examiner* — Mallika D Fairchild
(74) *Attorney, Agent, or Firm* — Ballard Spahr LLP

(57) ABSTRACT

An apparatus includes an outer adhesive layer comprising a conductive gel or conductive adhesive, at least one layer of anisotropic material, a layer of dielectric material, and a skin contact layer comprising a conductive gel or conductive adhesive. The at least one layer of anisotropic material and the layer of dielectric material are positioned between the outer adhesive layer and the skin contact layer. The layer of dielectric material contacts at least a first layer of the at least one layer of anisotropic material to form a capacitive structure.

20 Claims, 5 Drawing Sheets

APPARATUS COMPRISING DIELECTRIC LAYER COUPLED TO ANISOTROPIC LAYER

CROSS-REFERENCE TO RELATED APPLICATION

This application claims priority to and the benefit of the filing date of U.S. Provisional Patent Application No. 63/356,228, filed Jun. 28, 2022, the entirety of which is hereby incorporated by reference herein.

FIELD

This application relates to apparatuses for providing Tumor Treating Fields, the apparatuses having at least one layer of anisotropic material and a layer of dielectric material in contact with the anisotropic material.

BACKGROUND

Tumor Treating Fields (TTFields) therapy is a proven approach for treating tumors using alternating electric fields at frequencies between 50 kHz to 1 MHz, more commonly 100-500 KHz. The alternating electric fields are induced by electrode assemblies (e.g., arrays of capacitively coupled electrodes, also called transducer arrays) placed on opposite sides of a target location in the subject's body. When an AC voltage is applied between opposing electrode assemblies, an AC current is coupled through the electrode assemblies and into the subject's body.

SUMMARY

Disclosed herein, in one aspect, is an apparatus having an outer adhesive layer comprising a conductive gel or conductive adhesive, at least one layer of anisotropic material, a layer of dielectric material, and a skin contact layer comprising a conductive gel or conductive adhesive. The at least one layer of anisotropic material and the layer of dielectric material are positioned between the outer adhesive layer and the skin contact layer. The layer of dielectric material contacts at least a first layer of the at least one layer of anisotropic material to form a capacitive structure.

BRIEF DESCRIPTION OF THE DRAWINGS

Various embodiments are described in detail below with reference to the accompanying drawings, wherein like reference numerals represent like elements.

DETAILED DESCRIPTION

This application describes apparatuses (e.g., exemplary treatment assemblies) that can be used, e.g., for delivering TTFields to a subject's body and treating one or more cancers or tumors located in the subject's body.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

Introduction

Figure 1:
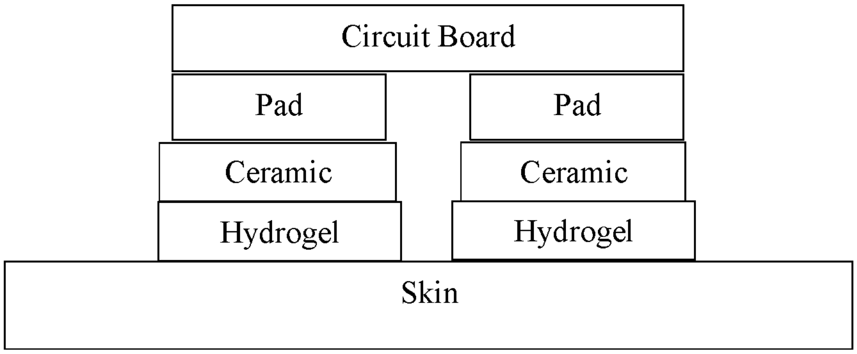
(Prior Art) FIG. 1
FIG. 1 is a cross sectional view of a known electrode assembly for providing TTFields.

FIG. 1 depicts a conventional apparatus for applying TTFields. As shown, the apparatus can include a circuit board, metallic pads coupled to the circuit board, ceramic discs positioned beneath the metallic pads to serve as a dielectric material, and skin contact layers comprising a hydrogel.

In the disclosed apparatuses, systems, and methods, the use of polymer films as the layer of dielectric material provides the promise of greater flexibility than the conventional ceramic discs, and therefore better conformability to the subject's skin, but high dielectric constant polymer films are delicate and are often pierced when adjacent to the metal pad, as well as in the cutting process during manufacture of the array. Furthermore, the high dielectric polymers are expensive and cheaper materials are needed. The apparatuses, systems, and methods disclosed herein provide a level of protection for the layer of dielectric material. Furthermore, in providing the disclosed apparatuses, systems, and methods with the dielectric material coupled to the layer(s) of anisotropic material, the area of contact to the capacitive layer can be the entire area of the layer(s) of anisotropic material. The increase in the area of the capacitor means that the dielectric material does not need to have as high a dielectric constant, so a cheaper material can be used (e.g., a less expensive polymer or a metal oxide, e.g. $Al_2O_3$, which could be applied by chemical vapor deposition, CVD, onto a substrate and is sufficiently flexible as a thin film).

The Apparatus

Disclosed herein, and with reference to FIGS. 2-5, is an apparatus 10 comprising an outer adhesive layer 20. The outer adhesive layer 20 can comprise a conductive gel or conductive adhesive 22. The apparatus 10 can further comprise at least one layer of anisotropic material 30, a layer of dielectric material 40, and a skin contact layer 50. The skin contact layer 50 can comprise a conductive gel or conductive adhesive 52. In some aspects, the layer of anisotropic material is a layer of nonmetallic anisotropic material.

The at least one layer of anisotropic material 30 and the layer of dielectric material 40 can be positioned between the outer adhesive layer 20 and the skin contact layer 50. The layer of dielectric material 40 can contact at least a first layer 30*a* of the at least one layer of anisotropic material 30 to form a capacitive structure 12.

Figure 2:
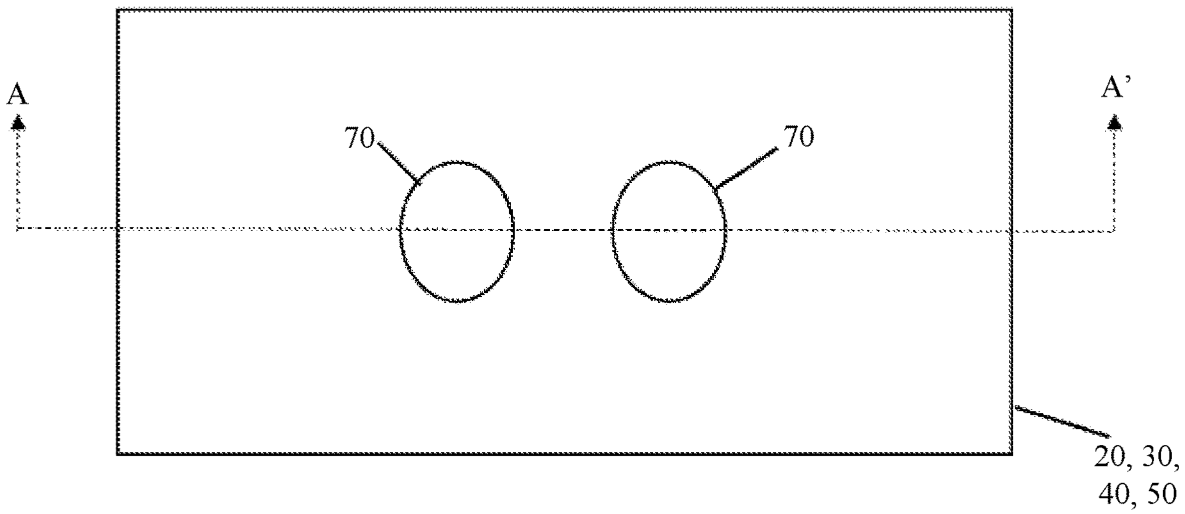
FIG. 2 is a schematic top view of an exemplary apparatus as disclosed herein.

In some aspects, the apparatus 10 can comprise a circuit board 60 (e.g., a printed circuit board (PCB) or flex circuit). The circuit board 60 can be electrically coupled to the outer adhesive layer 20. In some optional aspects, the circuit board 60 can be electrically coupled to the outer adhesive layer 20 through one or more conductive elements (e.g., metal pads 70) that are in electrical contact with the circuit board 60. In FIG. 2, two metal pads 70 are shown, but additional electrode elements can be included in the apparatus 10. In alternative embodiments, the apparatus 10 includes only a single electrode element (e.g., a single metal pad 70).

In some optional aspects, the layer of dielectric material 40 and the first layer of anisotropic material 30*a* can have surface areas that are each greater than a total surface area of the at least one metal pad 70. For example, the surface areas of the layer of dielectric material 40 and the first layer of anisotropic material 30*a* can be at least twice (e.g., about 3-5 times greater than) the total surface area of the at least one metal pad.

In some aspects, the layer of anisotropic material 30 can comprise a sheet of anisotropic material 32 having a rear face 34 and a front face 36 (the front face facing toward the subject's skin). The sheet of anisotropic material 32 can have a first thermal conductivity in a direction that is perpendicular to the front face 36. In some aspects, the thermal conductivity of the sheet in directions that are parallel to the front face can be more than two times higher than the first thermal conductivity. In further aspects, the sheet of anisotropic material 32 can have a first resistance in a direction that is perpendicular to the front face, and the resistance of the sheet in directions that are parallel to the front face can be less than half of the first resistance.

In some optional aspects, the first layer of anisotropic material 30*a* can comprise graphite.

Optionally, the first layer of anisotropic material 30*a* can comprise a synthetic graphite.

In further optional aspects, the first layer of anisotropic material 30*a* can comprise a sheet of pyrolytic graphite or graphitized polymer film.

In further optional aspects, the first layer of anisotropic material 30*a* can comprise graphite foil. For example, optionally, the first layer of anisotropic material can comprise graphite foil made from compressed high purity exfoliated mineral graphite.

The layer of dielectric material 40 can have a skin-facing surface 42 and an opposing outwardly facing surface 44. The first layer of anisotropic material 30*a* can have a skin-facing surface 38*a* and an opposing outwardly facing surface 39*a*.

Figure 3:
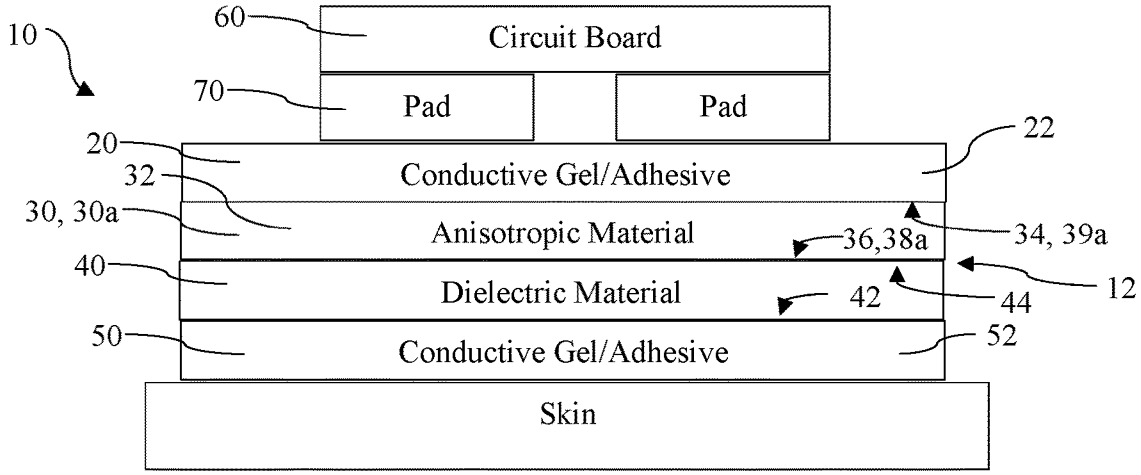
FIG. 3 is an exemplary cross sectional view of the apparatus of FIG. 2, taken at line A-A'.

In some aspects, and as shown in FIG. 3, the outwardly facing surface 44 of the dielectric material 40 can contact the skin-facing surface 38*a* of the first layer of anisotropic material 30*a*. In some embodiments, and as shown in FIG. 3, the outwardly facing surface 39*a* of the first layer of anisotropic material 30*a* can contact the outer adhesive layer 20. In further aspects, and as shown in FIG. 3, the skin-facing surface 42 of the layer of dielectric material 40 can contact the skin contact layer 50.

Figure 4:
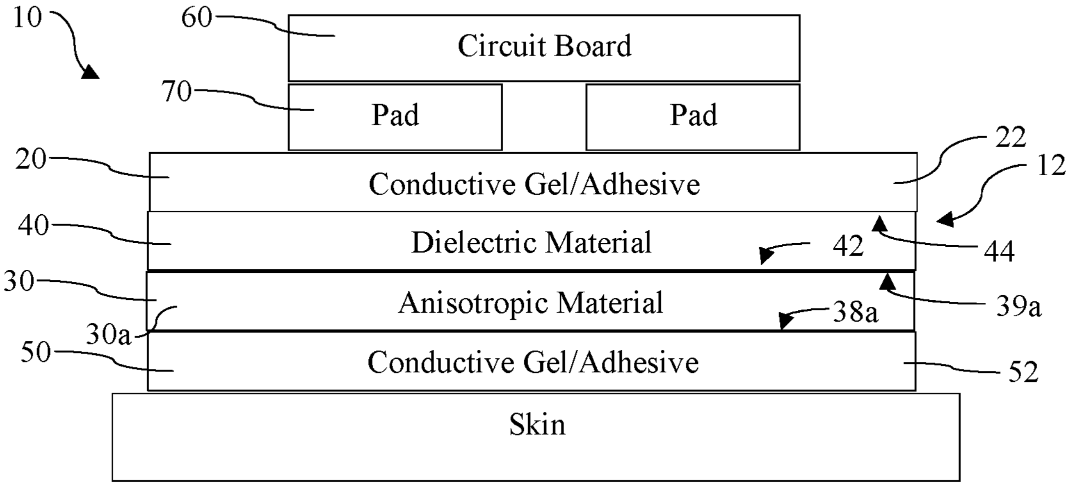
FIG. 4 is another exemplary cross sectional view of the apparatus of FIG. 2, taken at line A-A'.

In some aspects, and as shown in FIG. 4, the skin-facing surface 42 of the dielectric material 40 can contact the outwardly facing surface 39*a* of the first layer of anisotropic material 30*a* to form the capacitive structure 12. In some optional aspects, the outwardly facing surface 44 of the dielectric material 40 can contact the outer adhesive layer 20 (e.g. conductive gel or conductive adhesive 22). In some embodiments, the skin-facing surface 38*a* of the first layer of anisotropic material 30*a* can contact the skin contact layer 50. The embodiments of FIG. 4 show the relative positioning of the layer of anisotropic material 30*a* and the dielectric material layer 40 reversed between the outer adhesive layer 20 and the skin contact layer 50 compared with the FIG. 3 embodiments. In some such FIG. 4 embodiments, the relative positioning of the other components in the apparatus 10, such as the circuit board 60 and the metal pads 70, can be unchanged.

Figure 5:
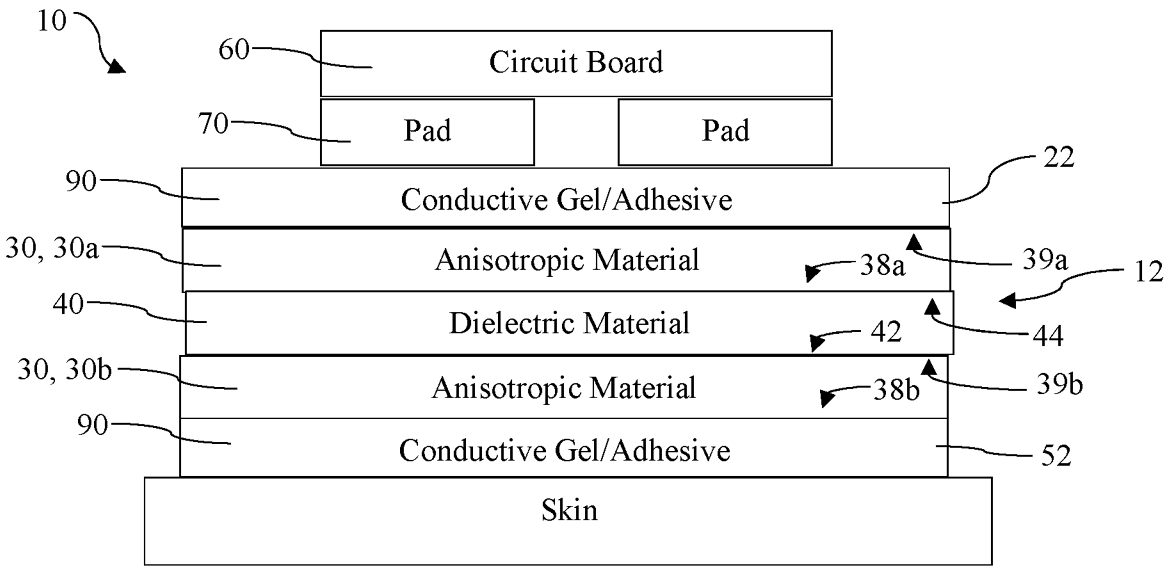
FIG. 5 is yet another exemplary cross sectional view of the apparatus of FIG. 2, taken at line A-A'.

Referring to FIG. 5, in some optional aspects, the at least one layer of anisotropic material 30 can comprise a second layer of anisotropic material 30*b*. The layer of dielectric material 40 is positioned between the first and second layers of anisotropic material 30*a,b*, forming a capacitive structure 12. The second layer of anisotropic material 30*b* can have a skin-facing surface 38*b* and an opposing outwardly facing surface 39*b*. In some aspects, the outwardly facing surface 39*a* of the first layer of anisotropic material 30*a* can contact the outer adhesive layer 20. In further aspects, the skin-facing surface 42 of the layer of dielectric material 40 can contact the outwardly facing surface 39*b* of the second layer of anisotropic material 30*b*. In still further aspects, the skin-facing surface 38*b* of the second layer of anisotropic material 38*b* can contact the skin contact layer 50.

In some optional aspects, the layer of dielectric material 40 can be positioned between and contact both the first and second layers of anisotropic material 30*a,b* (FIG. 5). In these aspects, other than the 3-layer sandwich structure (first layer of anisotropic material 30*a*-dielectric material layer 40-second layer of anisotropic material 30*b*), the relative positioning of the other components in the apparatus 10, such as the circuit board 60 and the metal pads 70, can be unchanged.

Figure 6:
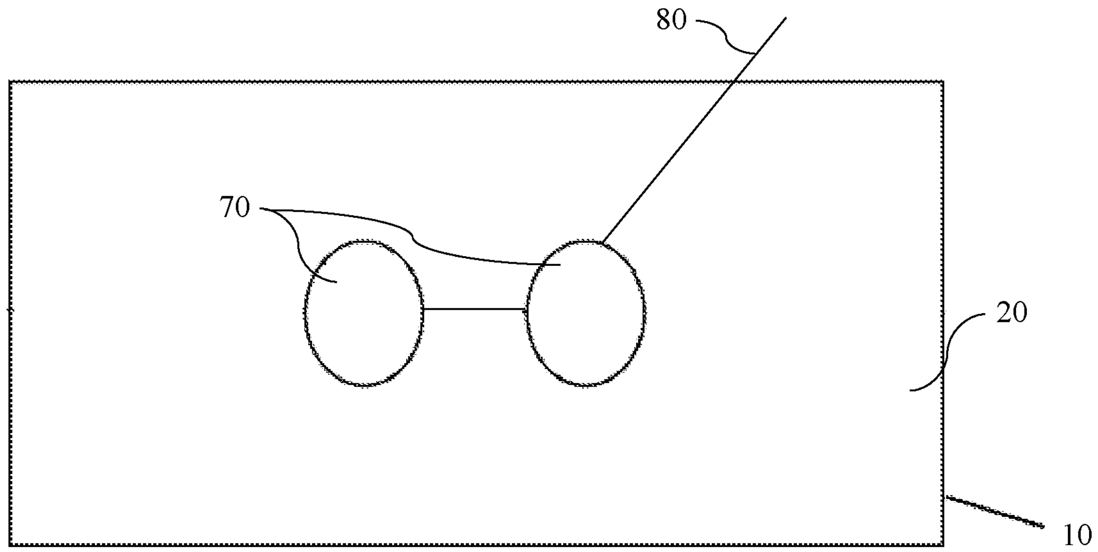
FIG. 6 is a schematic top view of an exemplary apparatus as disclosed herein.

Referring to FIG. 6 (and earlier FIGS. 3-5), in some optional aspects, the apparatus can comprise a wire 80 that is electrically coupled to the outer adhesive layer 20. Optionally, in these aspects, the apparatus 10 does not comprise a circuit board 60 or flex circuit. Optionally, the wire 80 can be coupled to the outer adhesive layer 20 via one or more metal pads 70 or via a metal layer. Optionally, and in the alternative, the apparatus 10 does not comprise a metal pad 70 or a metal layer. Optionally, the wire 80 can be coupled to the outer adhesive layer 20 via a circuit board 60 or flex circuit. Such embodiments can exist for each of the embodiments described herein.

Figure 7:
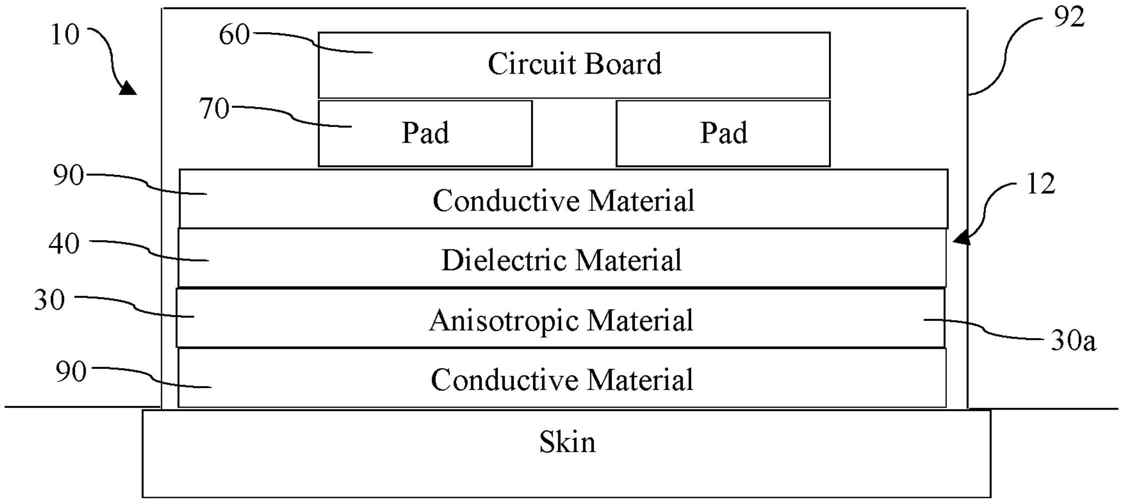
FIG. 7 is a cross sectional view of an exemplary apparatus as disclosed herein.

Referring to FIG. 7, the apparatus 10 can comprise at least one layer of anisotropic material 30 and a layer of dielectric material 40. The layer of dielectric material 40 can contact at least a first layer 30*a* of the at least one layer of anisotropic material 30 to form a capacitive structure 12.

The at least one layer of anisotropic material 30 and the layer of dielectric material 40 can be positioned between opposed layers of conductive materials 90 (e.g., the outer adhesive layer 20 and the skin contact layer 50, shown in FIGS. 3-4). In various aspects, the conductive materials 90 can optionally comprise conductive gel or conductive adhesive. In further aspects, the conductive materials 90 can comprise conductive grease. In these aspects, a cover 92 (e.g., a bandage, plaster, or other covering structure) can retain the assembly 10 in a stacked arrangement and against the skin of the patient. Optionally, a bandage or other cover 92 may be utilized in any of the embodiments described herein. Other than replacing the conductive gel or conductive adhesive of the outer adhesive layer with a conductive grease, and the optional addition of a bandage or cover 92, the FIG. 7 embodiment resembles that of the FIG. 4 embodiment, and the relative positioning of the other components in the apparatus 10, such as the circuit board 60 and the metal pads 70, can be unchanged. Indeed, the replacement of the conductive gel or conductive adhesive of the outer adhesive layer with a conductive grease, and the optional addition of a bandage or cover 92, can also be employed as an additional embodiment for any and all of the other embodiments described herein. Moreover, the replacement of the conductive gel or conductive adhesive of the skin contact layer with a conductive grease, and the optional addition of a bandage or cover 92, can also be employed as an additional embodiment for any and all of the other embodiments described herein.

Exemplary embodiments disclosed herein incorporate into the apparatus a sheet of material having anisotropic thermal properties and/or anisotropic electrical properties (referred to herein also as the layer of anisotropic material 30). If the sheet of material has anisotropic thermal properties (e.g., greater in-plane thermal conductivity than perpendicular to the plane), then the sheet spreads the heat out more evenly over a larger surface area. If the sheet of material has anisotropic electrical properties (e.g., greater in-plane electrical conductivity than perpendicular to the plane; or, conversely, lower in-plane resistance than perpendicular to the plane), then the sheet spreads the current out more evenly over a larger surface area. In each case, this lowers the temperature of the hot spots and raises the temperature of the cooler regions when a given AC voltage is applied to the apparatus. Accordingly, the current can be increased (thereby increasing the therapeutic effect) without exceeding the safety temperature threshold at any point on the subject's skin.

In some embodiments, the anisotropic material is anisotropic with respect to electrical conductivity properties. In some embodiments, the anisotropic material is anisotropic with respect to thermal conductivity properties. In some embodiments, the anisotropic material is anisotropic with respect to both electrical conductivity properties and thermal conductivity properties.

The anisotropic thermal properties include directional thermal properties. Specifically, the sheet has a first thermal conductivity in a direction that is perpendicular to its front face. And the thermal conductivity of the sheet in directions parallel to the front face is more than two times higher than the first thermal conductivity. In some preferred embodiments, the thermal conductivity in the parallel directions is more than ten times higher than the first thermal conductivity. For example, the thermal conductivity of the sheet in directions that are parallel to the front face can be more than: 1.5 times, 2 times, 3 times, 5 times, 10 times, 20 times, 100 times, 200 times, or even more than 1,000 times higher than the first resistance.

The anisotropic electrical properties include directional electrical properties. Specifically, the sheet has a first resistance in a direction that is perpendicular to its front face. And resistance of the sheet in directions parallel to the front face is less than the first resistance. In some preferred embodiments, the resistance in the parallel directions is less than half of the first resistance or less than 10% of the first resistance. For example, the resistance of the sheet 70 in directions that are parallel to the front face can be less than: 75%, 50%, 40%, 30%, 20%, 10%, 5%, 1%, 0.5%, or even less than 0.1% of the first resistance.

In some embodiments (e.g., when the sheet of anisotropic material is a sheet of pyrolytic graphite), the sheet of anisotropic material has both anisotropic electrical properties and anisotropic thermal properties.

In some optional aspects, the layer of anisotropic material is a layer of nonmetallic anisotropic material. Use of nonmetallic anisotropic material is particularly advantageous in situations where preventing the transfer of ions into a subject's body is desirable. More specifically, using a metallic sheet could result in the transfer of ions into a subject's body.

In some optional aspects, the layer of dielectric material 40 can comprise a high dielectric constant polymer. In alternative aspects, the dielectric material 40 can be a ceramic material. In alternative aspects, the dielectric material 40 can be a metal oxide, e.g. $Al_2O_3$, which could be applied by chemical vapor deposition, CVD, onto a substrate and is sufficiently flexible as a thin film.

In various optional aspects, the layer of dielectric material 40 can have a dielectric constant ranging from 10 to 50,000.

In some preferred embodiments, the high dielectric polymer material 40 comprises poly(vinylidene fluoride-trifluoroethylene-chlorotrifluoroethylene) and/or poly(vinylidene fluoride-trifluoroethylene-1-chlorofluoroethylene). Those two polymers are abbreviated herein as "Poly(VDF-TrFE-CTFE)" and "Poly(VDF-TrFE-CFE)," respectively. The dielectric constant of these materials is on the order of 40. In some embodiments, the polymer layer can be poly (vinylidene fluoride-trifluoroethylene-chlorotrifluoroethylene-chlorofluoroethylene) or "Poly(VDF-TrFE-CTFE-CFE)."

In some embodiments, the terpolymer used in the insulating polymer layer can comprise VDF, TrFE, CFE and/or CTFE in any suitable molar ratio. Suitable terpolymers include those, for example, having 30 to 80 mol % VDF, 5 to 60 mol % TrFE, with CFE and/or CTFE constituting the balance of the mol % of the terpolymer In all of the embodiments disclosed herein, it is preferred that the layer of dielectric material should completely cover the area of the layer of anisotropic material (or the layer of dielectric material, in combination with one or more other insulating materials, should completely cover or substantially completely cover the area of the layer of anisotropic material) in order for the dual layer to act as a capacitive structure. Thus, in exemplary aspects, it is contemplated that a surface area of the layer of dielectric material (or a surface area of the dielectric material in combination with other insulating materials) can be greater or equal to surface area(s) of the layer(s) of anisotropic material, with the dimensions of the layer(s) of anisotropic material being less than or equal to corresponding dimensions of the layer(s) of dielectric material such that a periphery of the anisotropic material does not extend beyond a periphery of the dielectric material.

Although complete coverage of the anisotropic material is preferred, it is contemplated that other embodiments can include configurations in which the dielectric material substantially covers the area of the anisotropic material. As used herein, the term "substantially cover" refers to configurations in which the dielectric material (or dielectric material in combination with other insulating materials) covers at least 90% or at least 95% or at least 99% of the surface area of the anisotropic material.

Method of Using the Apparatus

Figure 8:
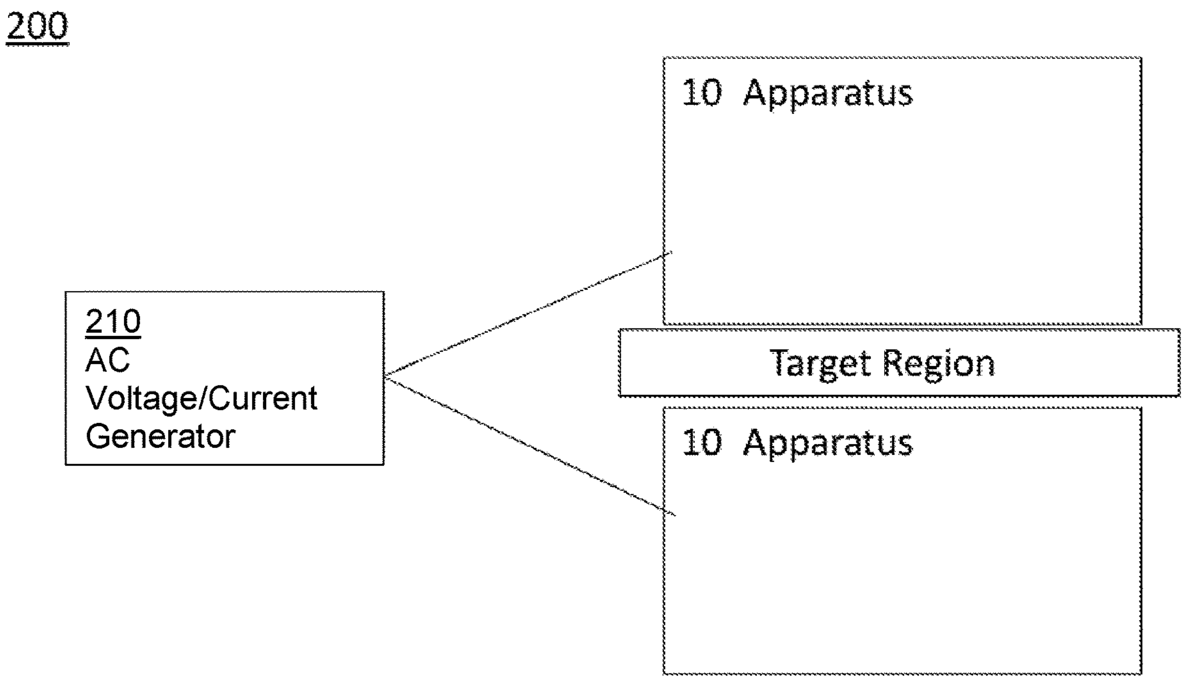
FIG. 8 is a block diagram of a system for using the apparatus as disclosed herein.

A method of using an apparatus 10 as disclosed herein can comprise using the apparatus 10 to generate an electrical field. FIG. 8 illustrates an exemplary system 200 for applying electrical fields using apparatuses 10 as disclosed herein. A plurality of apparatuses 10 (e.g., two apparatuses, as illustrated) can be positioned with a target region therebetween. An AC voltage or AC current generator 210 can be in communication with each apparatus 10. The AC voltage or AC current generator 210 can be configured to generate alternating electric fields through the target region.

The method can include positioning a first of the apparatuses 10 at a first position on or in the subject's body. For example, the apparatus 10 can be positioned on the subject's skin at the right of the subject's head facing a target region (e.g., a brain tumor).

A second of the apparatuses 10 can be positioned at a second position on or in the patient's body. For example, the second apparatus 10 can be positioned on the subject's skin at the left of the patient's head facing the target region.

An alternating voltage can be applied between the apparatuses 10. The applying can be implemented by applying the alternating voltage between (i) a first electrode element (e.g., a metal pad 70) disposed in electrical contact with the layer of anisotropic material 30 of the first apparatus 10 and (ii) a second electrode element disposed in electrical contact with the layer of anisotropic material 30 of the second apparatus 10.

In some embodiments, the frequency of the alternating voltage is between 50 kHz and 1 MHz, or between 100 kHz and 500 kHz. In some aspects, the AC voltage generator can be controlled by a controller. The controller can use temperature measurements to control the amplitude of the current to be delivered via the apparatuses 10 in order to maintain temperatures below a safety threshold (e.g., 41° C.). This can be accomplished, for example, by measuring a first temperature of a first electrode element, measuring a second temperature of a second electrode element, and controlling the applying of the alternating voltage based on the first temperature and the second temperature, as described below.

More specifically, temperature sensors (e.g., thermistors) can be positioned in thermal contact with respective electrode elements within each of the apparatuses 10. The temperature sensors can measure respective first and second temperatures (e.g., at first and second electrode elements in the first and second apparatuses 10, respectively), and the controller can control the output of the AC voltage generator based on these temperatures. The use of further temperature sensors positioned at additional electrode elements can measure temperatures at a plurality of electrode elements in the transducer array, and the controller can control the current applied to each electrode element according to a delta temperature compared to the threshold temperature (e.g., 41° C.), and thereby balance any temperature hot-spots on the array.

Advantages of the Disclosed Apparatus

The disclosed apparatus 10 can be more easily and inexpensively manufactured as compared to other configurations. The use of polymer films as the dielectric material 40 provides greater flexibility than the conventional ceramic discs, and therefore better conformability to the subject's skin, but the polymer films are delicate and are often pierced when adjacent to the metal pad 70, as well as in the cutting process during manufacture of the array. The dielectric material 40 can be protected by the layer(s) of anisotropic material 30, thereby increasing the durability of the dielectric material 40. Further, in providing the apparatus with the dielectric material 40 coupled to the layer(s) of anisotropic material 30, the area of contact to the capacitive layer can be the entire area of the layer(s) of anisotropic material 30. The increase in the area of the capacitor means that the dielectric polymer does not need to have as high a dielectric constant (polymers having a high dielectric constant are often more expensive than materials with lower dielectric constants), so a cheaper material can be used (e.g., a polymer or a metal oxide, e.g. $Al_2O_3$, which could be applied by chemical vapor deposition, CVD, onto a substrate and is sufficiently flexible as a thin film).

Apparatuses Having Layers that Comprise a Conductive Adhesive Composite

Optionally, the outer adhesive layer 20 and/or the skin contact layer 50 can comprise hydrogel. It is further contemplated that the outer adhesive layer 20 and/or the skin contact layer 50 can comprise conductive adhesive composites (described further below) rather than hydrogel.

In exemplary aspects, the conductive adhesive composite can comprise a dielectric material and conductive particles dispersed within the dielectric material. In some embodiments, at least a portion of the conductive particles define a conductive pathway through a thickness of the conductive adhesive composite. In some embodiments, it is contemplated that the conductive particles can be aligned in response to application of an electric field such that the conductive particles undergo electrophoresis. In some aspects, the dielectric material is a polymeric adhesive. Optionally, in these aspects, the polymeric adhesive can be an acrylic adhesive. In some aspects, the conductive particles can comprise carbon. Optionally, in these aspects, the conductive particles can comprise graphite powder. Additionally, or alternatively, the conductive particles can comprise carbon flakes. Additionally, or alternatively, the conductive particles can comprise carbon granules. Additionally, or alternatively, the conductive particles can comprise carbon nanotubes. Additionally, or alternatively, the conductive particles can comprise carbon black powder. In further aspects, the conductive adhesive composite further comprises a polar material (e.g., a polar salt). The polar salt can be a quaternary ammonium salt, such as a tetra alkyl ammonium salt. Exemplary conductive adhesive composites, as well as methods for making such conductive adhesive composites, are disclosed in U.S. Pat. Nos. 8,673,184 and 9,947,432, which are incorporated herein by reference for all purposes. In exemplary aspects, the conductive adhesive composite can be a dry carbon/salt adhesive, such as the OMNI-WAVE adhesive compositions manufactured and sold by FLEXCON (Spencer, MA, USA). In other exemplary aspects, the conductive adhesive composite can be an electrically conductive adhesive, such as the ARcare® 8006 electrically conductive adhesive composition manufactured and sold by Adhesives Research, Inc. (Glen Rock, PA, USA).

In exemplary aspects, the outer adhesive layer 20 and/or the skin contact layer 50 does not comprise hydrogel.

In further exemplary aspects, the skin contact layer 50 does not comprise a latex rubber polymer.

In further exemplary aspects, the skin contact layer 50 does not comprise silver or silver chloride.

In still further aspects, the conductive adhesive composite layer has a thickness ranging from about 30 μm to about 2000 μm, such as from 30 μm to about 200 μm. Optionally, the conductive adhesive composite in the outer adhesive layer can have a thickness ranging from about 30 μm to about 2000 μm, or from about 50 μm to about 1000 μm, or from about 50 μm to about 200 μm, or from about 70 μm to about 150 μm. Optionally, the conductive adhesive composite in the skin contact layer can have a thickness ranging from about 30 μm to about 100 μm, or from about 30 μm to about 70 μm, or from about 40 μm to about 60 μm, or from about 45 μm to about 55 μm.

In still further aspects, the conductive adhesive composite does not comprise water.

In exemplary aspects, the conductive particles of the conductive adhesive composite comprise a plurality of groups of conductive particles. In these aspects, the conductive particles of the combined groups of conductive particles can be aligned to define a respective conductive pathway through the thickness of the conductive in the adhesive composite electrode assemblies.

Optionally, in exemplary aspects, the apparatus can further comprise a release liner that covers the skin contact layer. In these aspects, it is contemplated that, prior to use, the apparatus can be provided with the release liner to ensure that the skin contact layer does not adhere to undesirable surfaces or locations. Immediately prior to use, the release liner can be removed, and the skin contact layer can be positioned in contact with the skin of the patient.

In exemplary aspects, by using a conductive adhesive composite as a skin contact layer as disclosed herein, it is contemplated that additional backing and/or cover layers (such as, for example self-adhesive backing) can be omitted. In these aspects, it is contemplated that the conductive adhesive composite can provide sufficient adhesion to the skin such that it is unnecessary to provide additional layers to maintain a desired position of the apparatus on the body of the subject, thereby improving ease of use and decreasing the overall cost of manufacture and use.

In further aspects, by avoiding the use of hydrogel within an apparatus as disclosed herein, it is contemplated that electrode assemblies comprising conductive adhesive composites as disclosed herein do not require moisture barrier packaging, thereby making the cost of packaging far more affordable. Additionally, it is contemplated that the conductive adhesive composites of the disclosed electrode assemblies can avoid the signal variation issues of hydrogels, thereby providing consistent material properties (e.g., tackiness) and reliable performance during delivery of TTFields. Further, it is contemplated that the disclosed conductive adhesive composites can have a far greater shelf life than hydrogels, thereby decreasing the frequency at which electrode assemblies (or the skin contact layers of electrode assemblies) must be replaced.

It is further contemplated that embodiments that include the sheet of anisotropic material can additionally aid in avoiding or reducing overheating of the electrodes and associated discomfort on the skin by dissipating both electrical current and heat in a lateral (in-plane) direction rather than passing directly through the layer (in a direction perpendicular to the plane of the skin contact layer) in a concentrated manner.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus comprising:

an outer adhesive layer comprising a conductive gel or conductive adhesive;

at least one layer of anisotropic material;

a layer of dielectric material; and a skin contact layer comprising a conductive gel or conductive adhesive, wherein the at least one layer of anisotropic material and the layer of dielectric material are positioned between the outer adhesive layer and the skin contact layer, and wherein the layer of dielectric material contacts at least a first layer of the at least one layer of anisotropic material to form a capacitive structure.

Aspect 2: The apparatus of aspect 1, further comprising a circuit board or flex circuit, wherein the circuit board or flex circuit is electrically coupled to the outer adhesive layer.

Aspect 3: The apparatus of aspect 2, wherein the circuit board or flex circuit is electrically coupled to the outer adhesive layer through at least one metal pad that is in electrical contact with the circuit board or flex circuit.

Aspect 4: The apparatus of aspect 3, wherein the layer of dielectric material and the first layer of anisotropic material have surface areas that are each greater than a total surface area of the at least one metal pad.

Aspect 5: The apparatus of any one of the preceding aspects, wherein the first layer of anisotropic material comprises a sheet of anisotropic material having a front face and a rear face, the sheet having a first thermal conductivity in a direction that is perpendicular to the front face, wherein thermal conductivity of the sheet in directions that are parallel to the front face is more than two times higher than the first thermal conductivity, or the sheet has a first resistance in a direction that is perpendicular to the front face, wherein resistance of the sheet in directions that are parallel to the front face is less than half of the first resistance.

Aspect 6: The apparatus of any one of the preceding aspects, wherein the first layer of anisotropic material comprises graphite.

Aspect 7: The apparatus of any one of the preceding aspects, wherein the first layer of anisotropic material comprises a synthetic graphite.

Aspect 8: The apparatus of any one of the preceding aspects, wherein the first layer of anisotropic material comprises a sheet of pyrolytic graphite or graphitized polymer film.

Aspect 9: The apparatus of aspect 6, wherein the first layer of anisotropic material comprises graphite foil.

Aspect 10: The apparatus of aspect 9, wherein the first layer of anisotropic material comprises graphite foil made from compressed high purity exfoliated mineral graphite.

Aspect 11: The apparatus of any one of the preceding aspects, wherein the layer of dielectric material has a skin-facing surface and an opposing outwardly facing surface, wherein the first layer of anisotropic material has a skin-facing surface and an opposing outwardly facing surface, and wherein the outwardly facing surface of the dielectric material contacts the skin-facing surface of the first layer of anisotropic material.

Aspect 12: The apparatus of aspect 11, wherein the outwardly facing surface of the first layer of anisotropic material contacts the outer adhesive layer.

Aspect 13: The apparatus of aspect 11 or aspect 12, wherein the skin-facing surface of the layer of dielectric material contacts the skin contact layer.

Aspect 14: The apparatus of any one of aspects 1-10, wherein the layer of dielectric material has a skin-facing surface and an opposing outwardly facing surface, wherein the first layer of anisotropic material has a skin-facing surface and an opposing outwardly facing surface, and wherein the skin-facing surface of the layer of dielectric material contacts the outwardly facing surface of the first layer of anisotropic material.

Aspect 15: The apparatus of aspect 14, wherein the outwardly facing surface of the layer of dielectric material contacts the outer adhesive layer.

Aspect 16: The apparatus of aspect 14 or aspect 15, wherein the skin-facing surface of the first layer of anisotropic material contacts the skin contact layer.

Aspect 17: The apparatus of any one of aspects 1-10, wherein the at least one layer of anisotropic material further comprises a second layer of anisotropic material, and wherein the layer of dielectric material is positioned between the first and second layers of anisotropic material.

Aspect 18: The apparatus of aspect 17, wherein the layer of dielectric material has a skin-facing surface and an opposing outwardly facing surface, wherein the first layer of anisotropic material has a skin-facing surface and an opposing outwardly facing surface, wherein the second layer of anisotropic material has a skin-facing surface and an opposing outwardly facing surface, and wherein the outwardly facing surface of the first layer of anisotropic material contacts the outer adhesive layer.

Aspect 19: The apparatus of aspect 18, wherein the skin-facing surface of the layer of dielectric material contacts the outwardly facing surface of the second layer of anisotropic material.

Aspect 20: The apparatus of aspect 18 or aspect 19, wherein the skin-facing surface of the second layer of anisotropic material contacts the skin contact layer.

Aspect 21: The apparatus of any one of aspects 17-20, wherein the layer of dielectric material is positioned between and contacts both the first and second layers of anisotropic material.

Aspect 22: The apparatus of any one of the preceding aspects, wherein the layer of dielectric material comprises a dielectric polymer. The dielectric polymer may have a dielectric constant of greater than 10, such as from 10 to 50,000.

Aspect 23: The apparatus of any one of aspects 1-21, wherein the dielectric material is a ceramic material.

Aspect 24: The apparatus of any one of aspects 1-21, wherein the dielectric material is a metal oxide.

Aspect 25: The apparatus of any one of the preceding aspects, wherein the dielectric material has a dielectric constant ranging from 10 to 50,000.

Aspect 26: The apparatus of aspect 1, further comprising a wire that is electrically coupled to the outer adhesive layer.

Aspect 27: The apparatus of aspect 26, wherein the apparatus does not comprise a circuit board or flex circuit.

Aspect 28: An apparatus comprising:

at least one layer of anisotropic material;

a layer of dielectric material, wherein the layer of dielectric material contacts at least a first layer of the at least one layer of anisotropic material to form a capacitive structure; and opposed layers of conductive material, wherein the at least one layer of anisotropic material and layer of dielectric material are positioned between the opposed layers of conductive material.

Aspect 29: An apparatus of aspect 28, wherein the conductive material of at least one layer of the opposed layers of conductive material is a conductive adhesive.

Aspect 30: An apparatus of aspect 28, wherein the conductive material of at least one layer of the opposed layers of conductive material is a conductive gel.

Aspect 31: An apparatus of any one of aspects 28-30, wherein the conductive material of at least one layer of the opposed layers of conductive material is a conductive grease.

Aspect 32: An apparatus of aspect 28, wherein the conductive material of at least one layer of the opposed layers of conductive material is a conductive gel or a conductive adhesive.

Aspect 33: The apparatus of any one of aspects 28-32, further comprising a cover that is configured to hold the capacitive structure against skin of a patient.

Aspect 34: A method comprising: generating an electric field using the apparatus of any one of the preceding aspects.

Aspect 35: The method of aspect 34, wherein the electric field is an alternating electric field having a frequency of from 50 kHz to 1 MHz, or from 100 kHz to 500 kHz.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus comprising:

an outer adhesive layer comprising a conductive gel or conductive adhesive;

at least one layer of anisotropic material, wherein the at least one layer of anisotropic material has a front face and a rear face, and the at least one layer of anisotropic material has one or both of (i) a first thermal conductivity in a direction that is perpendicular to the front face and thermal conductivity in directions that are parallel to the front face more than two times higher than the first thermal conductivity, and (ii) a first resistance in a direction that is perpendicular to the front face and resistance in directions that are parallel to the front face less than half of the first resistance;

a layer of dielectric material; and a skin contact layer comprising a conductive gel or conductive adhesive;

wherein the at least one layer of anisotropic material and the layer of dielectric material are positioned between the outer adhesive layer and the skin contact layer, and wherein the layer of dielectric material contacts at least a first layer of the at least one layer of anisotropic material to form a capacitive structure.

2. The apparatus of claim 1, further comprising:

a circuit board or flex circuit, wherein the circuit board or flex circuit is electrically coupled to the outer adhesive layer.

3. The apparatus of claim 2, wherein the circuit board or flex circuit is electrically coupled to the outer adhesive layer through at least one metal pad that is in electrical contact with the circuit board or flex circuit.

4. The apparatus of claim 3, wherein the layer of dielectric material and the first layer of anisotropic material have surface areas that are each greater than a total surface area of the at least one metal pad.

5. The apparatus of claim 1, wherein the first layer of anisotropic material comprises graphite.

6. The apparatus of claim 1, wherein the first layer of anisotropic material comprises a sheet of pyrolytic graphite or a graphitized polymer film, or graphite foil made from compressed high purity exfoliated mineral graphite.

7. The apparatus of claim 1, wherein the layer of dielectric material has a skin-facing surface and an opposing outwardly facing surface, wherein the first layer of anisotropic material has a skin-facing surface and an opposing outwardly facing surface, and wherein the outwardly facing surface of the dielectric material contacts the skin-facing surface of the first layer of anisotropic material.

8. The apparatus of claim 7, wherein the outwardly facing surface of the first layer of anisotropic material contacts the outer adhesive layer.

9. The apparatus of claim 7, wherein the skin-facing surface of the layer of dielectric material contacts the skin contact layer.

10. The apparatus of claim 1, wherein the layer of dielectric material has a skin-facing surface and an opposing outwardly facing surface, wherein the first layer of anisotropic material has a skin-facing surface and an opposing outwardly facing surface, and wherein the skin-facing surface of the layer of dielectric material contacts the outwardly facing surface of the first layer of anisotropic material.

11. The apparatus of claim 10, wherein the outwardly facing surface of the layer of dielectric material contacts the outer adhesive layer.

12. The apparatus of claim 10, wherein the skin-facing surface of the first layer of anisotropic material contacts the skin contact layer.

13. The apparatus of claim 1, wherein the at least one layer of anisotropic material further comprises a second layer of anisotropic material, and wherein the layer of dielectric material is positioned between the first and second layers of anisotropic material.

14. The apparatus of claim 1, wherein the layer of dielectric material comprises a dielectric polymer or a metal oxide.

15. The apparatus of claim 1, wherein the at least one layer of anisotropic material has a first thermal conductivity in a direction that is perpendicular to the front face and thermal conductivity in directions that are parallel to the front face more than two times higher than the first thermal conductivity.

16. The apparatus of claim 1, wherein the at least one layer of anisotropic material has a first resistance in a direction that is perpendicular to the front face and resistance in directions that are parallel to the front face less than half of the first resistance.

17. An apparatus comprising:

at least one layer of anisotropic material, wherein the at least one layer of anisotropic material has a front face and a rear face, and the at least one layer of anisotropic material has one or both of (i) a first thermal conductivity in a direction that is perpendicular to the front face and thermal conductivity in directions that are parallel to the front face more than two times higher than the first thermal conductivity, and (ii) a first resistance in a direction that is perpendicular to the front face and resistance in directions that are parallel to the front face less than half of the first resistance;

a layer of dielectric material, wherein the layer of dielectric material contacts at least a first layer of the at least one layer of anisotropic material to form a capacitive structure; and opposed layers of conductive material, wherein the at least one layer of anisotropic material and the layer of dielectric material are positioned between the opposed layers of conductive material.

18. The apparatus of claim 17, wherein the conductive material of at least one layer of the opposed layers of conductive material is a conductive gel or a conductive adhesive.

19. The apparatus of claim 17, wherein the conductive material of at least one layer of the opposed layers of conductive material is a conductive grease.

20. A method comprising:

generating an electric field using an apparatus comprising:

an outer adhesive layer comprising a conductive gel or conductive adhesive;

at least one layer of anisotropic material, wherein the at least one layer of anisotropic material has a front face and a rear face, and the at least one layer of anisotropic material has one or both of (i) a first thermal conductivity in a direction that is perpendicular to the front face and thermal conductivity in directions that are parallel to the front face more than two times higher than the first thermal conductivity, and (ii) a first resistance in a direction that is perpendicular to the front face and resistance in directions that are parallel to the front face less than half of the first resistance;

a layer of dielectric material; and a skin contact layer comprising a conductive gel or conductive adhesive;

wherein the at least one layer of anisotropic material and the layer of dielectric material are positioned between the outer adhesive layer and the skin contact layer, and wherein the layer of dielectric material contacts at least a first layer of the at least one layer of anisotropic material to form a capacitive structure.

* * * * *